United States Patent [19]

Winandy et al.

[11] Patent Number: 4,747,308

[45] Date of Patent: May 31, 1988

[54] METHOD AND APPARATUS FOR NONDESTRUCTIVELY DETERMINING THE DENSITY OF A PLURALITY OF CONTIGUOUS SEGMENTS OF A NONHOMOGENEOUS SPECIMEN

[75] Inventors: Jerrold E. Winandy, Mazomanie; Kent A. McDonald, Cross Plains; Steven G. Hankel, Madison, all of Wis.

[73] Assignee: The United States of America as represented by the Secretary of Agriculture, Washington, D.C.

[21] Appl. No.: 25,749

[22] Filed: Mar. 13, 1987

[51] Int. Cl.$^4$ ............................................ G01M 19/00
[52] U.S. Cl. ........................................ 73/432.1; 73/65
[58] Field of Search ...................... 73/432.1, 849, 433, 73/435, 65

[56] References Cited

U.S. PATENT DOCUMENTS 1,999,312  4/1935  Zeissl .
3,175,438  3/1965  Johnson .
3,319,053  5/1967  Roberts .
4,366,874  1/1983  Pidoux et al. ......................... 177/25
4,372,405  2/1983  Stuart ................................... 177/25

FOREIGN PATENT DOCUMENTS 390396  11/1973  U.S.S.R. .................................. 73/65

Primary Examiner—Jerry W. Myracle
Attorney, Agent, or Firm—M. Howard Silverstein

[57] ABSTRACT

Method and apparatus for nondestructively estimating density of contiguous segments along the length of a straight, elongated specimen which is uniform in cross-section and heterogeneous in density throughout its length comprising maintaining the specimen in a horizontal position by supporting it at two points near opposite ends of the specimen; measuring the downward force exerted by the specimen at one of the points while periodically moving the other support along the length of the specimen. The measurements are applied to a static equilibrium equation together with external dimensions to determine segment densities.

11 Claims, 2 Drawing Sheets

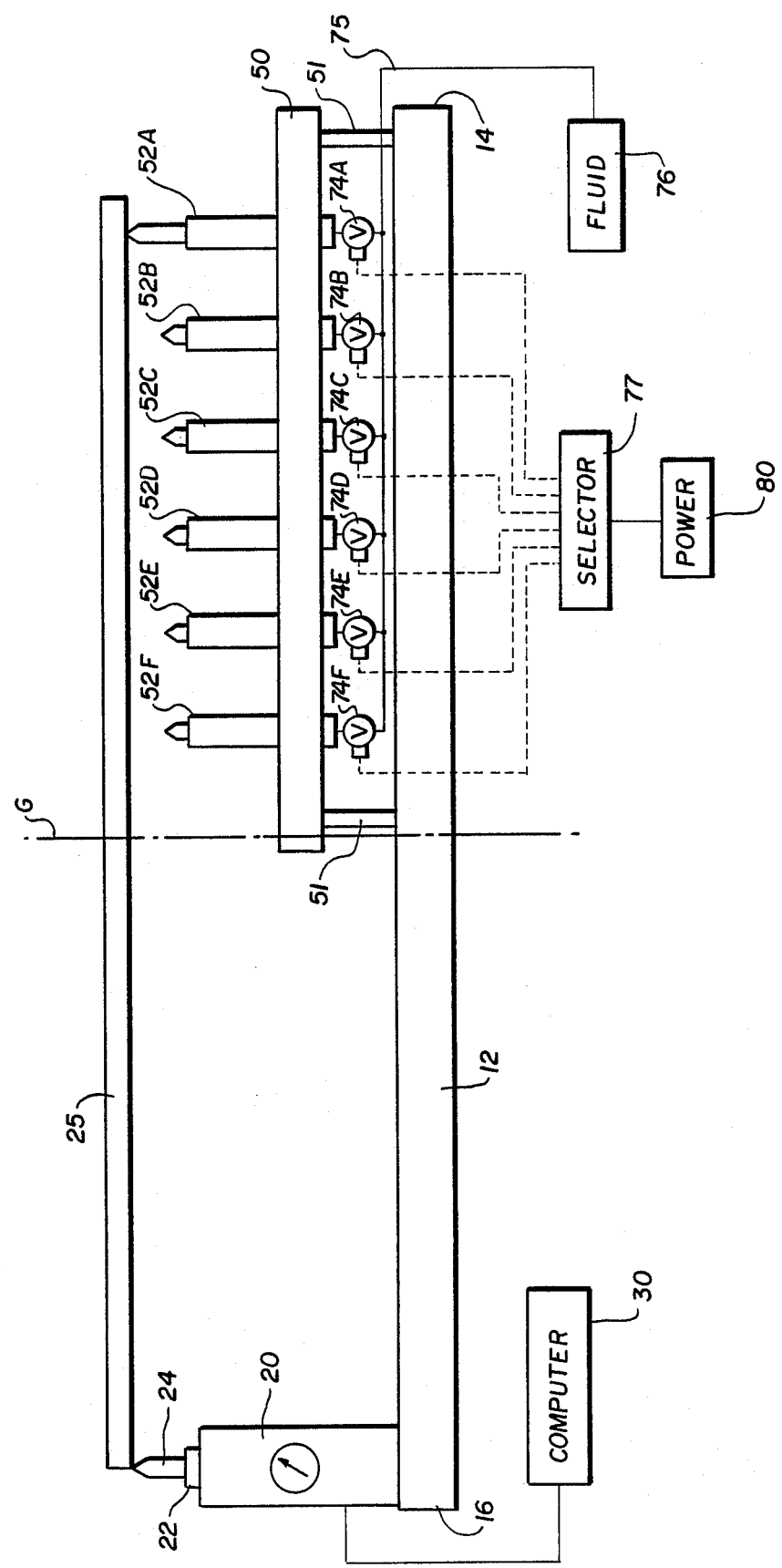

METHOD AND APPARATUS FOR NONDESTRUCTIVELY DETERMINING THE DENSITY OF A PLURALITY OF CONTIGUOUS SEGMENTS OF A NONHOMOGENEOUS SPECIMEN

TECHNICAL FIELD

The present invention relates generally to testing of lumber, and more particularly to a means and method for nondestructively determining the density of lumber. Most specifically, the present invention relates to means and method for nondestructively and accurately determining the density of a plurality of different areas within a piece of lumber whereby the nonhomogeneous nature of lumber is accounted for.

BACKGROUND ART

Present methods of grading structural lumber for strength include visual grading and machine grading. At best these methods only explain about 50 percent of the variability in strength because they do not entirely account for the heterogeneous nature of lumber. A piece of structural lumber is an assemblege of various lumber characteristics which range from clear, dense, straight-grained wood with high strength to knotty, low-density, cross-grained wood with low strength. The purpose of any grading method would be to account for these variations and assign a stress rating (i.e., a predicted strength level) to each piece. Visual stress rating is based primarily on an empirical estimation of the size of knots in each piece as they are limited by a specific grading rule. Inherent errors in judgment due to the physical demands on the visual grader lead to inaccurate assessments of lumber strength. More accurate estimates of the low-strength, low-density areas around knots are needed to improve upon this visual stress-rating method.

The machine stress-rating methods are an improvement over the visual approach, but also have some significant limitations. The most common machine stress-rating technique physically bends the lumber and measures its stiffness. Stress ratings, or predicted strength levels, are assigned to each based on established strength-to-stiffness relationships. This physical bending of the lumber, along with established visual limits (overrides) on knot sizes, leads to the final grade of the piece. A problem with this method is the large span required to adequately bend the piece and the inherent insensitivity of such a long span system to the short, low-strength, low-density, cross-grain areas often found in lumber. Therefore, this machine grading approach to grading structural lumber needs a more accurate estimate of the short, low-strength areas around knots before improved strength estimates are possible. The solution to this problem is specifically addressed by this invention.

Another, but less common, machine grading technique for structural lumber creates an energy wave within the piece and monitors the speed of the wave. A dynamic modulus of elasticity (MOE) is calculated as the product of wave speed and density. Taken over the full length of a lumber piece, an average MOE can be obtained from the wave speed and the density can be obtained from the size and weight of the specimen. More accuracy and a more desirable measurement of MOE would come about if the speed of the wave was obtained for short spans or short segments of the piece. This procedure would provide localized strength information for more accurate strength estimates. The problem that remains is to nondestructively obtain the short segment density needed for each short segment MOE calculation. The solution to this problem is specifically addressed by this invention.

Another important practical application of this invention is directed to an inherent problem associated with the waterborne preservative treatment of wood. Waterborne preservative treatments have been found to reduce the strength of many types of treated wood products. In lumber (nonclear specimens), strength reductions possibly as high as 25 percent are mentioned in ASTM D 245 (American Society for Testing and Materials 1978). This strength loss seems to be caused by both the hydrolytic chemicals and the temperature sustained in the subsequent kiln-drying process. It is suspected that kiln drying of waterborne preservative-treated lumber may significantly reduce its strength in localized areas. This reduction in strength is believed to be directly related to a reduction in density. Therefore, the solution, as stated previously, is to nondestructively obtain the short segment density. This is specifically addressed by this invention.

OBJECTS

It is a main object of the present invention to provide a new and improved means and method for accurately identifying low-density areas in lumber without presenting any significant risk of destroying or damaging that lumber being tested.

It is another object of the present invention to provide a new and improved means and method for nondestructively testing lumber which permits the accurate prediction of overall lumber density.

It is another object of the present invention to provide a new and improved means and method for nondestructively testing lumber in a rapid manner suitable for commercial application.

SUMMARY OF INVENTION

The present invention comprises a process and apparatus for nondestructively estimating weights of individual segments of a straight, elongated specimen having a uniform cross-section throughout its length, and further which exhibits heterogeneity as to density along its length, such as a piece of lumber.

Generally, the invention comprises (a) maintaining a specimen of predetermined weight and length in a horizontal position by supporting it at first and second points with first and second supports; wherein the first point is at or adjacent one end of the specimen; wherein the second point is near but not at the opposite end of the specimen; wherein that part of the specimen which extends from the second point to said opposite end defines a first specimen segment of predetermined length;

(b) measuring the downward force exerted by the specimen at the first point when the specimen is maintained in a horizontal position by support at the first and second points;

(c) determining the weight of the first segment in accordance with the following formula $$W_1 = (WT - 2(F_1))(L_s L_1)/L_s$$

where $W_1$ = weight of the first segment
$WT$ = total weight of the specimen
$F_1$ = measurement of the downward force at the first point
$L_1$ = length of the first segment
$L_s$ = length of the specimen In addition to determining weight, the segment's density also may be readily determined from a predetermined segment volume.

To determine weights or densities of additional segments, the invention further includes changing the second point of support to a third point of support to maintain the specimen in a horizontal position by support at the first and third points; wherein that part of specimen which extends between the second and third points defines a second segment of predetermined length; measuring the downward force exerted by the specimen at the first point when the specimen is maintained in a horizontal position by support at the first and third points; and determining the weight or density of the second segment in accordance with the following formula $$W_2 = (WT - 2(F_2))(L_s - L_1 - L_2)/L_s - W_1$$

where
$W_1$ = weight of the first segment
$w_2$ = weight of the second segment
$WT$ = total weight of the specimen
$F_2$ = measurement of the downward force at said first point when the specimen is supported at the first and third points
$L_1$ = length of the first segment
$L_2$ = length of the second segment
$L_s$ = length of the specimen By maintaining the support and measuring means at the first point, while changing the location of the other support means to points along almost half the length of the specimen, the weight and density of contiguous segments along said length of specimen may be determined. Thereafter, the specimen may be turned around, or the downward force measuring means may be switched to the opposite end of the specimen, in order to determine the weights and densities of contiguous segments on the remaining length of the specimen.

The above formulas are mathematical tools in applied mechanics for measuring stresses in horizontal beams having a homogeneous density. Because the specimen of the present invention has a heterogeneous density, and the internal moments (immeasurable internal stresses) will vary slightly, therefore in actuality these moments will not cancel out, as would be the case with a truly homogeneous material. Nonetheless, it has been discovered that the above formulas enable the determination of sufficiently accurate segment densities for one of the purposes of the present invention, namely to assist in more accurately assessing strength estimates of segments of a piece of lumber.

DRAWINGS

FIGS. 1a–e show the present invention in its simplest form.

FIG. 2 is an automated alternative embodiment.

DETAILED DESCRIPTION

Figure 1A:
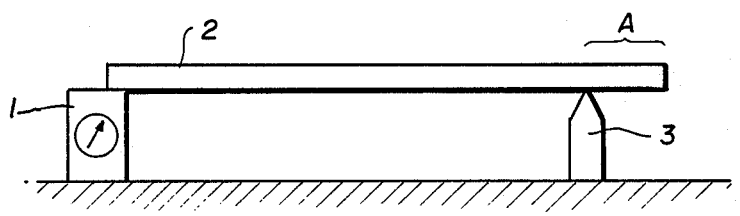

Referring to FIG. 1a, in its simplest form the apparatus of the present invention may comprise a scale 1 on which one end or first point of a specimen 2 is resting, and a rigid member 3 supporting the specimen at a second point to maintain the specimen in a horizontal position. That part of the specimen which extends from the second point to the right end of the specimen may be regarded as a first segment A.

The reading at scale 1 is combined with a predetermined total weight of the specimen and a predetermined length of segment A to determine a weight of segment A in accordance with the appropriate above formula. This weight readily is converted to a density measurement from a predetermined volume of segment A. (The predetermined total weight of specimen 2 may be obtained by first placing support member 3 at the right extremity of specimen 2.)

Figure 1B:
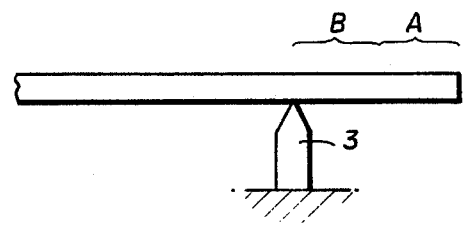

Next, as shown in FIG. 1b, support member 3 is moved to a third support point on the specimen, and a new reading is taken at the scale 1. This reading is combined with predetermined parameters and the first calculated weight measurement to determine weight or density of the second segment B.

Figure 1C:
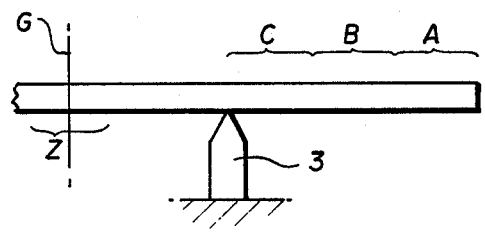

The process is repeated for segment C (FIG. 1c).

The formulas for calculating the weights of several segments on one side of a specimen's center of gravity may be represented by the following formulas:

$$W_1 = (WT - 2(F_1))(L_s - L_1)/L_s$$

$$W_2 = (WT - 2(F_2))(L_s - L_1 - L_2)/L_s - W_1$$

$$W_n = (WT - 2(F_n))(L_s - L_1 - L_2 \ldots - L_n)/L_s - W_1 - W_2 \ldots W_{n-1}$$

Figure 1D:
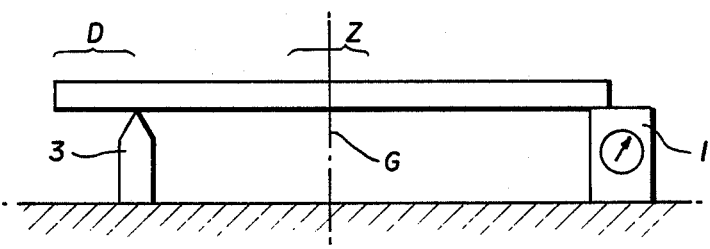
Figure 1E:
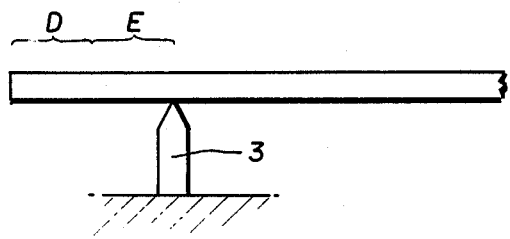

It will be seen that segment Z (FIG. 1c), which bridges across the center of gravity G of the specimen, is not measured at this time because the placement of support member 3 on the left end of segment Z will not maintain the specimen in a horizontal position. To complete the measurements of segments in the remaining length of the specimen, the scale may be placed on the right end of the specimen while the rigid support member 3 is placed near the left end (FIGS. 1d,e) thereby to determine weights or densities of segments D, E, and so on. Segment Z's weight may be lastly determined simply by substracting all the other segment weights from the total weight of the specimen.

Referring now to FIG. 2, therein is shown an automated embodiment of the present invention. The apparatus includes a base 12 having ends 14 and 16. A downward force measuring means or scale 20 located at end 16 includes a pan 22 having an upwardly extending first support means 24 mounted thereon. The signal from scale 20 is sent to computer equipment 30 including an interface, a computer and, for example, a printer. The other support means which cooperates with support 24 to maintain specimen 25 in a horizontal position is connected to a horizontal beam 50 near end 14 of base 12. Beam 50 stands on base 12 by means of legs 51, and is moveable along the base 12 in order to accomodate specimens of varying lengths.

Instead of moving one of the specimen supports as in FIGS. 1a–e from one predetermined point to another, in the embodiment of FIG. 2 there are a plurality of vertically moveable devices 52A–F connected to beam 50. In accordance with a predetermined sequence each one of the devices 52A–F is at its uppermost or support position while the remaining devices are retracted. Thus, assuming that device 52A, in cooperation with support 24, is supporting specimen 25 in a horizontal position for the purpose of obtaining a reading at scale 20, then the next step would be to retract or lower device 52A while raising device 52B to a support position.

Vertical movement of each device 52A-F is accomplished by a vertically-positioned, fluid actved piston inside a fixed cylindrical housing attached to beam 50. Specimen support rods are connected to the top of each piston. To cause gas or hydraulic liquid to enter the appropriate support device so as to raise a piston, and thereby to raise a support rod at the top of the piston, to its uppermost or support point, there are provided a plurality of solenoid valves 74A-F in the parallel fluid lines which connect each piston to a common fluid supply line 75 and fluid source 76.

A manual or computer-controlled selector 77 powered, for example, by a power supply 80, activates each solenoid valve 74A-F, and thereby activates each support device 54A-F, at the appropriate time. As a new support device is activated, a previous support device is deactivated by venting hydraulic support therefor through an exhaust port on its respective solenoid.

While the apparatus and process have been disclosed in conjunction with lumber testing, it can be applied to evaluate composite materials as well. Furthermore, while the device has been disclosed in conjunction with static testing, it can be converted into a continuous system by including a continuously moving reaction support in place of discrete lifting mechanisms, whereby the specimen is moved with respect to the support rather than moving the support with respect to the specimen as above described. A separate automatic feed system can be included so that each specimen is mechanically placed on the apparatus. The apparatus then would be converted into a production line device.

We claim:

1. A process for nondestructively estimating weights of individual segments of a straight, elongated specimen having a uniform cross-section and heterogeneous density along its length, and having a predetermined total weight and length comprising
    (a) maintaining said specimen in a horizontal position by supporting it at first and second points; wherein said first point is at or adjacent one end of said specimen; wherein said second point is near but not at the opposite end of said specimen; wherein that part of said specimen which extends from said second point to said opposite end defines a first specimen segment of predetermined length;
    (b) measuring the downward force exerted by said specimen at said first point when said specimen is maintained in said horizontal position by said first and second support points;
    (c) determining a weight for said first segment in accordance with the following formula $$W_1 = (WT - 2(F_1))(L_s - L_1)/L_s$$

where
    $W_1$ = weight of said first segment
    $WT$ = total weight of said specimen
    $F_1$ = measurement of said downward force at said first point
    $L_1$ = length of said first segment
    $L_s$ = length of said specimen 2. The process of claim 1 further comprising changing said second point of support to a third point of support to maintain said specimen in a horizontal position by supporting it at said first and third points; wherein that part of said specimen which extends between said second and third points defines a second segment of predetermined length;
    measuring the downward force exerted by said specimen at said first point when said specimen is maintained in said horizontal position by said first and third support points;
    determining a weight of said second segment in accordance with the following formula $$W_2 = (WT - 2(F_2))(L_s - L_1 - L_2)/L_s - W_1$$

where
    $W_1$ = weight of said first segment
    $W_2$ = weight of said second segment
    $WT$ = total weight of said specimen
    $F_2$ = measurement of said downward force at said first point when said specimen is supported by said first and third points
    $L_1$ = length of said first segment
    $L_2$ = length of said second segment
    $L_s$ = length of said specimen 3. The process of claim 2 further comprising maintaining said first point of support while continuing to change the point of support which cooperates with said first point to maintain said specimen in a horizontal position, wherein a plurality of contiguous segments on said specimen are defined by said changing points of support; continuing to measure the downward force at said first point after each change, and determining a weight of each of said continguous segments in accordance with the following formula $$W_n = (WT - 2(F_n))(L_s - L_1 - L_2 \ldots - L_n)/L_s - W_1 - W_2 \ldots - W_n$$

4. The process of claim 3 wherein the volume of each segment is predetermined, and wherein a density for each contiguous segment is determined from said determined weight and predetermined volume.

5. The process of claim 4 wherein said specimen is a piece of lumber.

6. The process of claim 5 wherein said density determinations are carried out until the densities of contiguous segments extending over almost half the length of the specimen have been determined; and thereafter changing said first point of support and point of measurement to said opposite end in order to determine densities of contiguous segments extending along the remaining length of said specimen.

7. An apparatus for nondestructively estimating weights of individuals segments of a straight, elongated specimen having a uniform cross-section and heterogeneous density along its length, and having a predetermined total weight and length, comprising
    a straight, elongated specimen having a uniform cross-section and heterogeneous density along its length, and having a predetermined total weight and length;
    means to support said specimen at first and second points in order to maintain it in a horizontal position; wherein said first point is at or adjacent one end of said specimen; wherein said second point is near but not at the opposite end of said specimen; wherein that part of said specimen which extends from said second point to said opposite end defines a first specimen segment of predetermined length;

means connected to said support means at said first point to measure the downward force exerted by said specimen at said first point when said specimen is maintained in a horizontal position by support at said first and second points; and means connected to said measuring means to determine a weight of said first segment in accordance with the following formula $$W_1 = (WT - 2(F_1))(L_s - L_1)/L_s$$

where
$W_1$ = weight of said segment
$WT$ = total weight of said specimen
$F_1$ = measurement of said downward force
$L_1$ = length of said segment
$L_s$ = length of said specimen 8. An apparatus for nondestructively estimating weights of individual segments of a straight, elongated specimen having a uniform cross-section and heterogeneous density along its length, and having a predetermined total weight and length, comprising means to support said specimen at first and second points in order to maintain it in a horizontal position; wherein said first point is at or adjacent one end of said specimen; wherein said second point is near but not at the opposite end of said specimen; wherein that part of said specimen which extends from said second point to said opposite end defines a first specimen segment of predetermined length;

means connected to said support means at said first point to measure the downward force exerted by said specimen at said first point when said specimen is maintained in a horizontal position by support at said first and second points; means connected to said measuring means to determine a weight of said first segment in accordance with the following formula $$W_1 = (WT - 2(F_1))(L_s - L_1)/L_s$$

means to change specimen support from said second point to a third point point on said specimen while maintaining said first point of support in order to maintain said specimen in a horizontal position; wherein that part of said specimen which extends between said second and third points defines a second segment of predetermined length; wherein said measuring means includes means to measure the downward force at said first point when said specimen is maintained in said horizontal position by support at said first and third points; and wherein said weight determination means includes means to determine a weight of said second segment in accordance with the following formula $$W_2 = (WT - 2(F_2))(L_s - L_1 - L_2)/L - W_1$$

where, in the above formulas,
$W_1$ = weight of first segment
$W_2$ = weight of second segment
$WT$ = total weight of specimen
$F_1$ = measurement of said downward force at said first point when said specimen is supported at said first and second points
$F_2$ = measurement of downward force at said first point when said specimen is supported at said first and third points
$L_1$ = length of said first segment
$L_2$ = length of said second segment
$L_s$ = length of said specimen 9. The apparatus of claim 8 further including means to continue changing support from one point to another while maintaining said support at said first point; wherein said measuring means includes means to measure the downward force at said first point after each of said changes; and wherein said weight determination means includes means to determine individual weights of contiguous segments along said specimen in accordance with the following formula $$W_n = (WT - 2(F_n))(L_s - L_1 - L_2 \ldots - L_n)/L_s - W_1 - W_2 \ldots - W_{n-1}$$

10. The apparatus of claim 9 wherein the volume of each of said segments is predetermined, and wherein said weight determination means includes means to convert said weight determination to a density determination.

11. The apparatus of claim 10 wherein said means to change said support comprises a plurality of separate vertically-extendable support devices; means to raise one of said devices at a time to a specimen support position; means to lower one device at a time from a specimen support position.

* * * * *